(12) United States Patent
Truckey

(10) Patent No.: US 10,893,855 B2
(45) Date of Patent: Jan. 19, 2021

(54) RETRACTOR SYSTEM AND RETRACTOR WITH DETACHABLE HANDLE

(71) Applicant: Thompson Surgical Instruments, Inc., Traverse City, MI (US)

(72) Inventor: Adam Truckey, Suttons Bay, MI (US)

(73) Assignee: THOMPSON SURGICAL INSTRUMENTS, INC., Traverse City, MI (US)

( * ) Notice: Subject to any disclaimer, the term of this patent is extended or adjusted under 35 U.S.C. 154(b) by 285 days.

(21) Appl. No.: 15/918,530

(22) Filed: Mar. 12, 2018

(65) Prior Publication Data

US 2018/0271509 A1    Sep. 27, 2018

Related U.S. Application Data

(60) Provisional application No. 62/476,928, filed on Mar. 27, 2017.

(51) Int. Cl.
*A61B 17/02* (2006.01)
*A61B 17/00* (2006.01)

(52) U.S. Cl.
CPC ...... *A61B 17/0218* (2013.01); *A61B 17/0206* (2013.01); *A61B 2017/0046* (2013.01); *A61B 2017/00367* (2013.01); *A61B 2017/00477* (2013.01)

(58) Field of Classification Search
CPC ............ A61B 17/0218; A61B 17/0206; A61B 2017/00477; A61B 2017/0046; A61B 2017/00367
See application file for complete search history.

(56) References Cited

U.S. PATENT DOCUMENTS

| | | | |
|---|---|---|---|
| 3,749,088 A | 7/1973 | Kohlmann | |
| 4,971,038 A | 11/1990 | Farley | |
| 5,902,233 A | 5/1999 | Farley et al. | |
| 5,931,777 A | 8/1999 | Sava | |
| 5,984,865 A | 11/1999 | Farley et al. | |
| 5,984,867 A | 11/1999 | Deckman et al. | |
| 6,036,641 A * | 3/2000 | Taylor .............. | A61B 17/00234 600/231 |

(Continued)

FOREIGN PATENT DOCUMENTS

| | | |
|---|---|---|
| EP | 1269922 | 1/2003 |
| ES | 2272170 | 4/2007 |

(Continued)

*Primary Examiner* — Kevin T Truong
*Assistant Examiner* — Tracy L Kamikawa
(74) *Attorney, Agent, or Firm* — McAndrews, Held & Malloy, Ltd.

(57) ABSTRACT

A retractor system includes a retractor blade and a handle assembly. The retractor blade includes a base portion, a blade extending from the base portion, and a handle mount affixed to the base portion. The handle assembly includes an attachment portion and a retaining rod. The attachment portion includes a slot configured to receive the handle mount, a first cavity adjoining the slot, a retaining member moveable along the first cavity, and a second cavity adjoining the first cavity. Advancement of the retaining rod through the second cavity and into the first cavity advances the retaining member into the slot and into engagement with the handle mount.

19 Claims, 8 Drawing Sheets

(56) References Cited

U.S. PATENT DOCUMENTS

| | | | |
|---|---|---|---|
| 6,468,207 B1 | 10/2002 | Fowler, Jr. | |
| 6,887,198 B2 * | 5/2005 | Phillips | A61B 17/02 |
| | | | 600/227 |
| 7,182,731 B2 * | 2/2007 | Nguyen | A61B 17/0206 |
| | | | 600/229 |
| 7,892,174 B2 * | 2/2011 | Hestad | A61B 17/0293 |
| | | | 600/210 |
| 8,114,020 B2 | 2/2012 | Fricke et al. | |
| 8,257,255 B2 | 9/2012 | Farley et al. | |
| 9,277,906 B2 * | 3/2016 | White | A61B 17/02 |
| 9,320,506 B2 | 4/2016 | Bertagnoli et al. | |
| 2002/0026101 A1 | 2/2002 | Bookwalter et al. | |
| 2002/0095071 A1 | 7/2002 | Farley | |
| 2003/0004401 A1 | 1/2003 | Ball et al. | |
| 2003/0069478 A1 | 4/2003 | Phillips et al. | |
| 2004/0129109 A1 | 7/2004 | Phillips et al. | |
| 2004/0199055 A1 | 10/2004 | Mulac et al. | |
| 2004/0249388 A1 | 12/2004 | Michelson | |
| 2005/0113645 A1 | 5/2005 | Sharratt et al. | |
| 2005/0177028 A1 | 8/2005 | Royce et al. | |
| 2005/0192484 A1 | 9/2005 | Sharratt et al. | |
| 2006/0224044 A1 | 10/2006 | Marchek et al. | |
| 2007/0270840 A1 | 11/2007 | Chin et al. | |
| 2008/0215081 A1 | 9/2008 | Hsueh et al. | |
| 2009/0221876 A1 | 9/2009 | Cobb et al. | |

FOREIGN PATENT DOCUMENTS

| | | |
|---|---|---|
| FR | 2690067 | 10/1993 |
| FR | 2807313 | 10/2001 |
| GB | 1570499 | 7/1980 |

\* cited by examiner

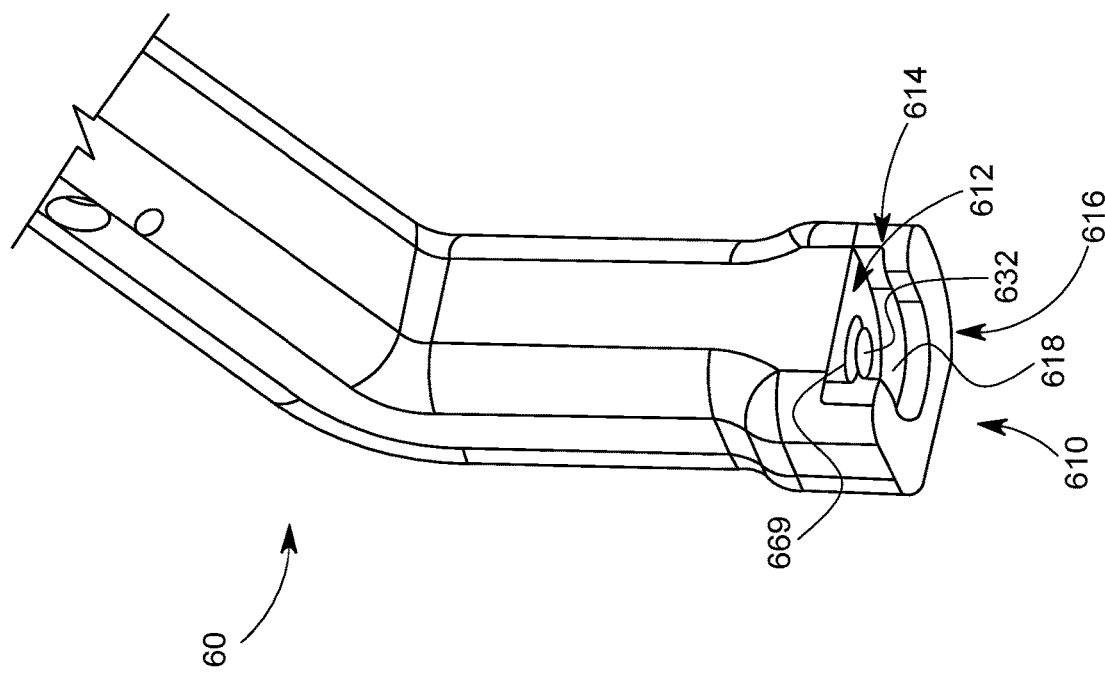

RETRACTOR SYSTEM AND RETRACTOR WITH DETACHABLE HANDLE

BACKGROUND

The present disclosure relates to a surgical apparatus that retracts soft tissue and other anatomy of a patient in order to provide access to an operative site.

During a surgical procedure, a surgeon may make an incision in a patient to access internal organs, bones, and/or other anatomical structures. Retraction devices may be used to hold back soft tissue and other patient anatomy in the immediate area of the incision. Such retraction devices may provide the surgeon with an unobstructed view of the internal organs, bones, and/or other anatomical structures. Furthermore, the retraction devices may provide the surgeon with an opening via which the surgeon may access the anatomical structures with one or more surgical tools.

Further limitations and disadvantages of conventional and traditional approaches will become apparent to one of skill in the art, through comparison of such approaches with the present disclosure as set forth in the remainder of the present application with reference to the drawings.

SUMMARY

Various aspects of this disclosure provide a retractor system comprising retractors that retract anatomy to provide exposure of an operative site. For example and without limitation, various aspects of this disclosure are directed to a retractor having a handle that may be used to manipulate and position a retractor blade. After positioning the retractor blade, the handle may be detached and removed in order to provide less encumbered access to the operative site.

BRIEF DESCRIPTION OF THE DRAWINGS

FIG. 4 provides a perspective view of an attachment portion of the handle assembly of FIG. 3A.

DETAILED DESCRIPTION

Figure 1:
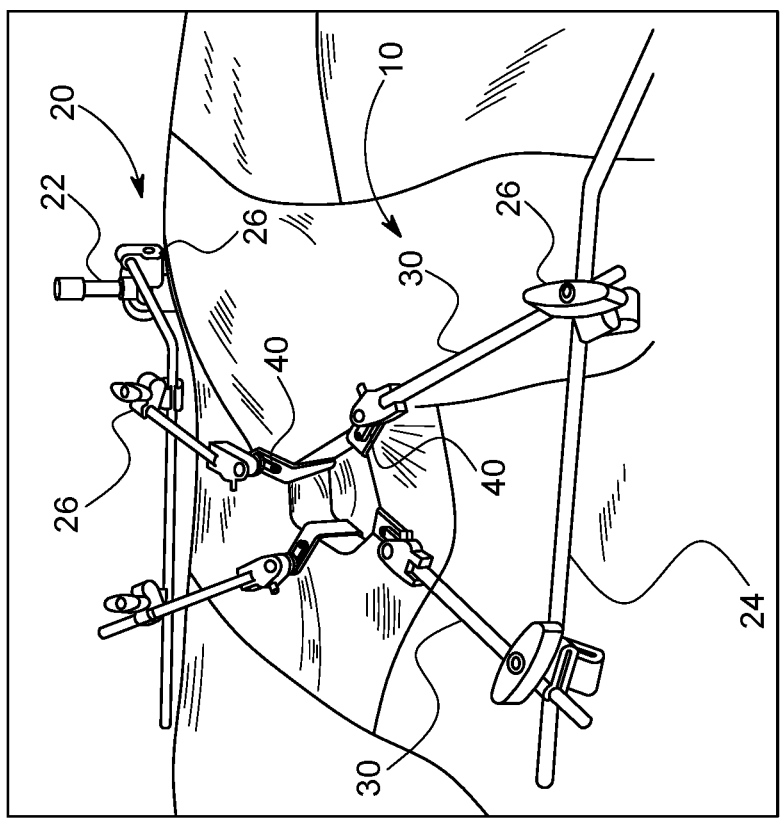
FIG. 1 provides a perspective view of a retractor system in accordance with various aspects of the present disclosure.

The following discussion presents various aspects of the present disclosure by providing examples thereof. Such examples are non-limiting, and thus the scope of various aspects of the present disclosure should not necessarily be limited by any particular characteristics of the provided examples. In the following discussion, the phrases "for example," "e.g.," and "exemplary" are non-limiting and are generally synonymous with "by way of example and not limitation," "for example and not limitation," and the like.

As utilized herein, "and/or" means any one or more of the items in the list joined by "and/or". As an example, "x and/or y" means any element of the three-element set {(x), (y), (x, y)}. In other words, "x and/or y" means "one or both of x and y." As another example, "x, y, and/or z" means any element of the seven-element set {(x), (y), (z), (x, y), (x, z), (y, z), (x, y, z)}. In other words, "x, y and/or z" means "one or more of x, y, and z."

The terminology used herein is for the purpose of describing particular examples only and is not intended to be limiting of the disclosure. As used herein, the singular forms are intended to include the plural forms as well, unless the context clearly indicates otherwise. It will be further understood that the terms "comprises," "includes," "comprising," "including," "has," "have," "having," and the like when used in this specification, specify the presence of stated features, integers, steps, operations, elements, and/or components, but do not preclude the presence or addition of one or more other features, integers, steps, operations, elements, components, and/or groups thereof.

It will be understood that, although the terms first, second, etc. may be used herein to describe various elements, these elements should not be limited by these terms. These terms are only used to distinguish one element from another element. Thus, for example, a first element, a first component or a first section discussed below could be termed a second element, a second component or a second section without departing from the teachings of the present disclosure. Similarly, various spatial terms, such as "upper," "lower," "side," and the like, may be used in distinguishing one element from another element in a relative manner. It should be understood, however, that components may be oriented in different manners, for example a semiconductor device may be turned sideways so that its "top" surface is facing horizontally and its "side" surface is facing vertically, without departing from the teachings of the present disclosure. Additionally, the term "on" will be utilized in the document to mean both "on" and "directly on" (e.g., with no intervening layer).

In the drawings, various dimensions (e.g., layer thickness, width, etc.) may be exaggerated for illustrative clarity. Additionally, like reference numbers are utilized to refer to like elements through the discussions of various examples.

The discussion will now refer to various example illustrations provided to enhance the understanding of the various aspects of the present disclosure. It should be understood that the scope of this disclosure is not limited by the specific characteristics of the examples provided and discussed herein.

FIG. 1 illustrates an embodiment of a retractor system 10 in accordance with various aspects of the present disclosure. The retractor system 10 may include a frame assembly 20, a jointed arm 30, and a plurality of retractor blades 40. The various components of the retractor system 10 may be made, for example, of stainless steel.

The frame assembly 20 may include one or more posts 22, frame arms 24, and clamps 26. Each post 22 may be fixed to a rail and/or a hospital bed (not shown) such that the post 22 extends upward in a generally vertical direction. Each post 22 may provide a location to which a frame arm 24 may be secured. In the illustrated embodiment, two posts 22 are secured on opposite sides of a hospital bed, with a frame arm 24 secured to each post 22 by a clamp 26. In the illustrated embodiment, the frame arms 24 are bent to extend toward the center of the hospital bed along a portion of their length.

The frame arms 24 may occupy a generally horizontal plane, and may provide a location to which to mount other components of the retractor system 10, such as jointed arms 30 via additional clamps 26.

Figure 2:
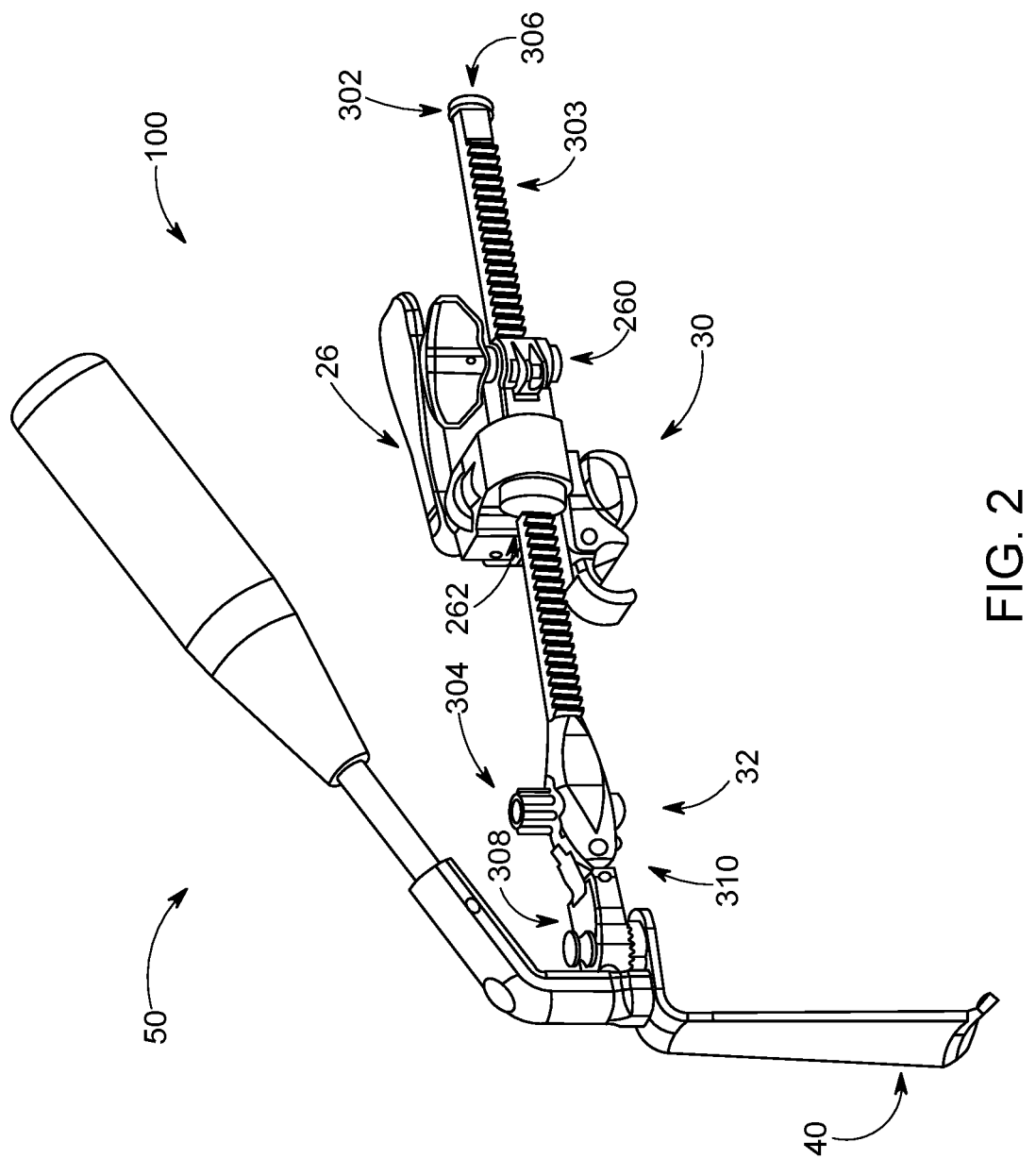
FIG. 2 provides a perspective view of a retractor assembly of FIG. 1 in accordance with various aspects of the present disclosure.

FIG. 2 illustrates a retractor assembly 100 comprising a retractor blade 40 and handle assembly 50 that are secured to a jointed arm 30 and clamp 26. The jointed arm 30 is adapted to provide for adjustable constraint of a proximal end of a retractor blade 40 when the retractor blade 40 is secured to the jointed arm 30. In some embodiments, the jointed arm 30 may provide at least some appreciable freedom of motion in at least one direction for the retractor blade 40 relative to the frame assembly 20. While preventing at least some motion of the retractor blade 40, the jointed arm 30 may allow the proximal end of the retractor blade 40 some freedom of motion but maintain the retractor blade 40 at or near a selected position. In other embodiments, the jointed arm 30 may be adapted to maintain the retractor blade 40 in a fixed or stationary position once various joints are arranged in a desired position.

The illustrated jointed arm 30 is an example of an adjustable arm used to secure a retractor blade 40 to the retractor frame assembly 20. The jointed arm 30 may comprise one or more single-axis hinges 32, which may be adjusted and then locked to a desired position. However, the jointed arm 30 may comprise other types of adjustable joints. For example, the jointed arm 30 may include one or more a universal joints, ball joints, prismatic joints, etc. located along the length of the jointed arm 30.

As shown, the jointed arm 30 may comprise an elongated shaft 306 that extends from a proximal end 302 toward a distal end 304. A head 308 may be adjoined to the distal end 304 of the shaft 306 via a pivot 310. The shaft 306 may further include a rack 303 adapted to engage a pinion 260 of a clamp 26 that is used secured the jointed arm 30 to the frame arm 24. Furthermore, the head 308 may be adapted to received and secure the retractor blade 40 to the shaft 306.

The shaft 306 may comprise a generally straight, generally cylindrical member. In some embodiments, the shaft 306 may be bent in one or more locations, or curved to accommodate different procedures or access sites. As noted above, the shaft 306 may include a rack 303. The rack 303 may be positioned along one or more longitudinal sides of the shaft 306 and may extend along such sides of the shaft 306. Moreover, the rack 303 may be sized such that the rack 303 passes through an aperture 262 in the clamp 26 such that teeth 305 of the rack 303 engage corresponding teeth (not shown) of the pinion 260. Due to such engagement of the rack 303 and the pinion 260, the pinion 260 may be actuated in order to adjust an amount that the distal end 304 of the shaft 306 extends from the frame arm 24. Namely, rotation of the pinion 206 in a first direction may extend the distal end 304 away from the frame arm 24. Conversely, rotation of the pinion 206 in a second direction opposite the first direction may retract the distal end 304 toward the frame arm 24.

Figure 5:
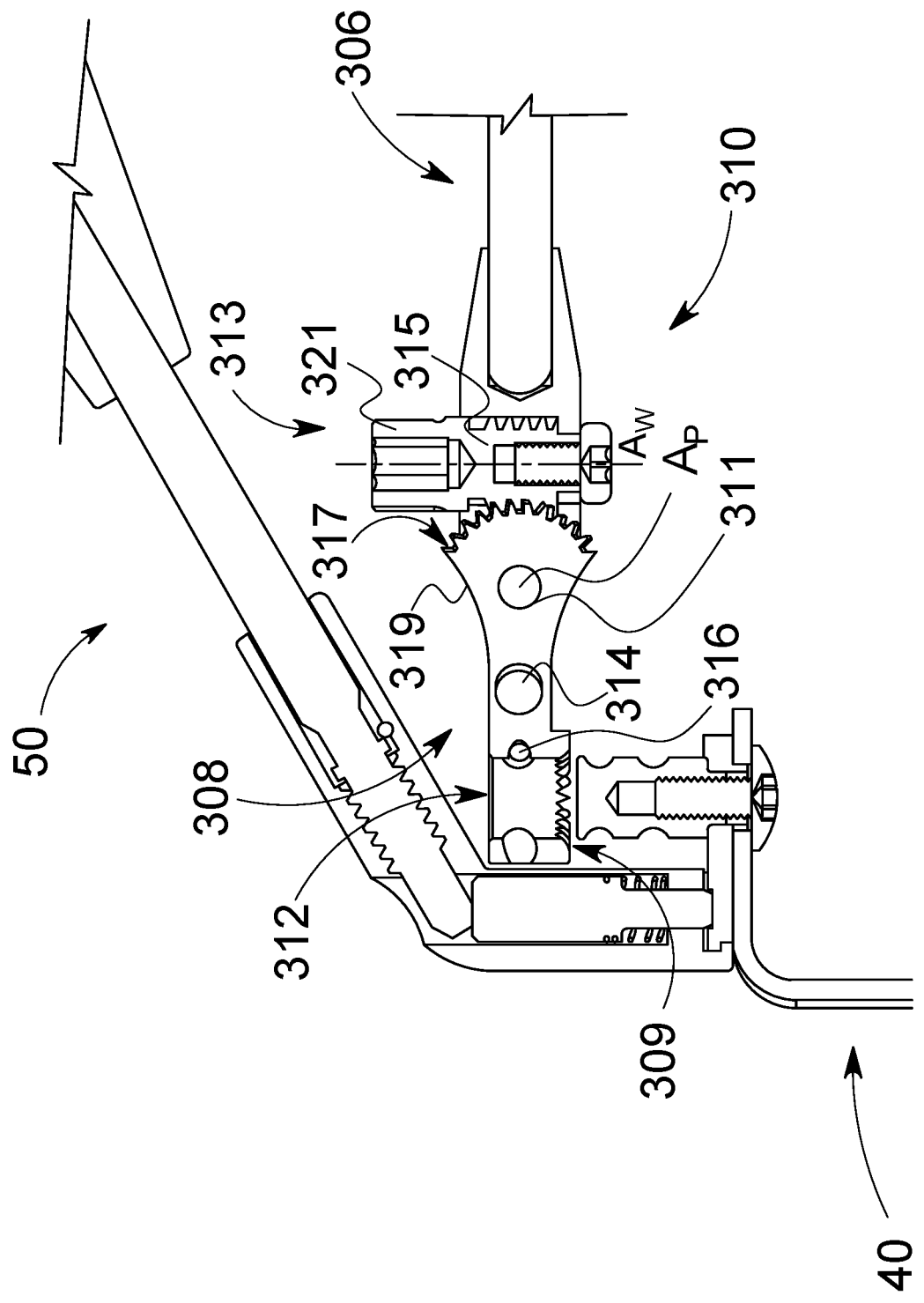
FIG. 5 provides a cross-sectional view of a retractor blade of FIG. 2 with a locked handle assembly as the retractor blade is being attached to a jointed arm of the retractor assembly.

Referring now to FIG. 5, the pivot 310 generally joins the head 308 to the shaft 306, allowing the shaft 306 and the head 308 to be adjusted relative to one another in one plane, but restricting their freedom of motion in other directions. For example, the pivot 310 may comprise a pin 311 that passes through aligned barrel holes of the shaft 306 and the head 308. The pivot 310 may further comprise a worm drive 313. The worm drive 313 may control and adjust the amount of pivot or angle between the shaft 306 and head 308. In particular, a thumb screw or worm 315 of the worm drive 313 may pass through the distal end 304 of the shaft 306 such that a longitudinal axis $A_W$ of the worm 315 is perpendicular to the longitudinal axis $A_P$ of the pin 311. Furthermore, a worm gear 317 of the worm drive 313 may be position along the proximal end 319 of the head 306 such that teeth of the worm gear 317 mesh with threads of the thumb screw or worm 315. Rotation of the worm 315 via the head 321 in a first direction may adjust or force the head 306 in a downward direction with respect to the shaft 306. Conversely, rotation of the worm 315 in a second direction opposite the first direction may adjust or force the head 306 in an upward direction with respect to the shaft 306.

The head 308 may include an attachment hole 312, an actuating button 314, and a locking ball 316. In the illustrated embodiment, the attachment hole 312, actuating button 314, and locking ball 316 cooperate to form an attachment mechanism. Through the use of an internal mechanism (not shown), depressing the actuating button 314 allows increased freedom of movement of the locking ball 316, which permits a post or other structure to be inserted into or removed from the attachment hole 312. Releasing the actuating button 314 constrains the locking ball 316 such that the locking ball 312 protrudes into the attachment hole 312 and secures an attachment post of the retractor blade 40. Thus, the retractor blade 40 may be secured to the shaft 306 via the head 308.

Aspects of the retractor blade 40 and handle assembly 50 are described below with to the exploded view of FIG. 3A and the detailed perspective view of FIG. 3B. The illustrated retractor blade 40 includes a blade 400 having a distal end 402, a proximal end 404, a retracting portion 406. The retractor blade 40 may further include a base portion 420 having an attachment post 410 and a handle mount 416. The distal end 402 may correspond to the end of the blade 400 oriented more deeply inside the patient during a surgical procedure, and the proximal end 404 may correspond to the end of the blade 400 oriented closer to a practitioner during a surgical procedure.

The retracting portion 406 generally extends from the proximal end 404 adjoined to the base portion 420 to the distal end 402. The base portion 420 may extend at an angle (e.g., 90°) from the retracting portion 406. The retracting portion 406 may be sized and adapted to hold back tissue from a site of interest during a procedure. In certain embodiments, a retractor system may include a number of differently sized and/or shaped retractor blades 40 to provide increased adaptability for different procedures and/or patients.

The base portion 420, located proximate to the proximal end 404, may provide a location or locations to grasp and/or secure the retractor blade 40. Located proximate to the base portion 420 are the attachment post 410 and the handle mount 416. The attachment post 410 may be sized and adapted to provide a location for attachment to the jointed arm 30. In particular, the attachment post 410 may be sized and adapted to cooperate with the attachment hole 312 of the head 308. To this end, the attachment post 410 may have a generally cylindrical-shape and may extend from an upper surface 422 of the base portion 420. In one embodiment, a longitudinal axis $A_A$ of the attachment post 410 extends at a right angle from the upper surface 422; however, the attachment post 410 in some embodiments may extend from the upper surface 422 at other angles.

As shown the attachment post 410 may include an upper annular groove 412 and a lower annular groove 414. The post 410 and grooves 412, 414 may be sized such that the attachment post 410 may pass freely through the attachment hole 312 of the head 308 when the locking ball 316 of the head 308 is not constrained, but may be held in place when one of a respective groove 412, 414 is aligned with the locking ball 316 and the locking ball 316 is constrained to protrude into the attachment hole 312.

The upper groove 412 may provide an attachment location that results in the upper surface 422 of the base portion 420 being slightly farther away from a lower surface of the head 308. In particular, the upper groove 412 may be sized and adapted such that when the upper groove 412 is aligned and constrained by the locking ball 316, the attachment post 410 is constrained from moving vertically with respect to the head 308. However, the upper groove 412, attachment hole 308, and locking ball 316 are sized and adapted such that the attachment feature 410 may rotate about the longitudinal axis $A_A$ with respect to the head 308.

As shown, the lower groove 414 is located nearer to the base portion 420 than the upper groove 412. As such, the upper surface 422 of the base portion 420 as well as the lower surface 309 of the head 308 may have cooperating serrated surfaces that restrict rotation of the attachment post 410 relative to the head 308 when the lower groove 414 accepts the locking ball 316. Thus, by using either the upper groove 412 or the lower groove 414, a practitioner may alter the amount of freedom of movement of the retractor blade 40 relative to the head 308.

The handle mount 416 may be sized and adapted to provide a location for attachment of a manipulator or handle that a practitioner may use to position the retractor blade 40. In the illustrated embodiments, the handle mount 416 may comprise generally, flat tab 418 having an upper surface 411 and a lower surface 413 that both extend perpendicularly from the attachment post 410 and parallel to the upper surface 422 of the base portion 420. A pedestal 419 (See, FIGS. 6 and 7) may affix the lower surface 413 to the upper surface 422 of the base portion 420 to provide the tab 418 with greater structural support. In particular, the pedestal 419 has a smaller width and length than the tab 418 such that lateral sides 421 and a distal end 423 of the tab 418 extend beyond the pedestal 419.

The tab 418 on the pedestal 419 may therefore define grooves 417 between the lower surface 413 of the tab 418 and the upper surface 422 of the base portion 420. In particular, the grooves 417 may traverse along the lateral sides 421 of the tab 418 and may traverse parallel along the upper surface 422. As explained below, the handle assembly 50 may be attached to the retractor blade 40 via a slidable engagement of the handle assembly 50 along the grooves 417. To this end, the distal end 423 of the tab 418 may be rounded or tapered to ease insertion of the tab 418 into an attachment portion 60 of the handle assembly 50. Furthermore, the upper surface 422 of the tab 418 may include a recess 425 with vertical walls 427. The recess 425 is sized to receive a retaining member 630 (See, FIGS. 6 and 7) of the handle assembly 50. When received, the retaining member 630 may engage the walls 427 of the recess 425 and prevent removal of the tab 418 from the attachment portion 60 of the handle assembly 50, thereby locking the handle assembly 50 to the retractor blade 40.

Figure 3A:
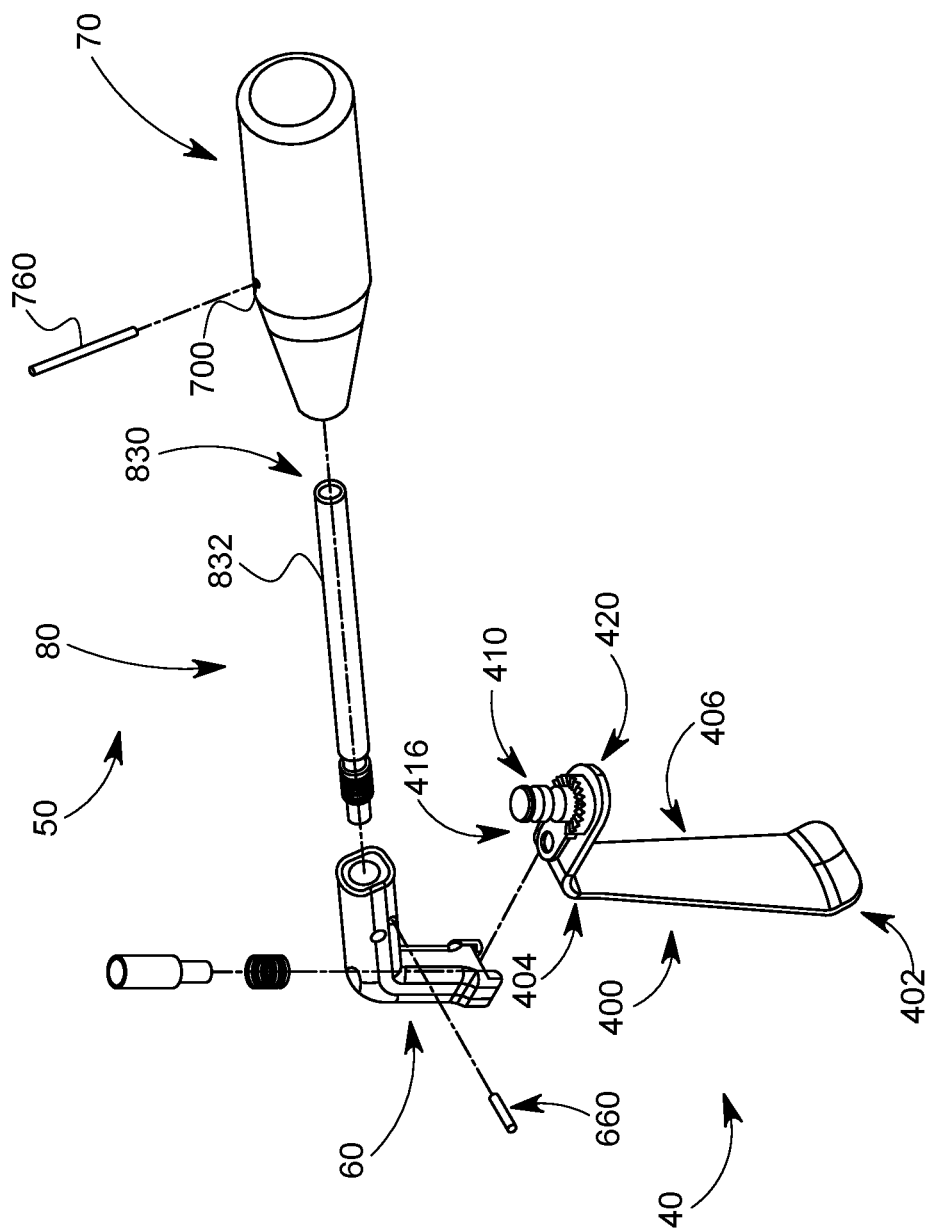
FIG. 3A provides an exploded view of a handle assembly in regard to a retractor blade of FIG. 2.
Figure 3B:
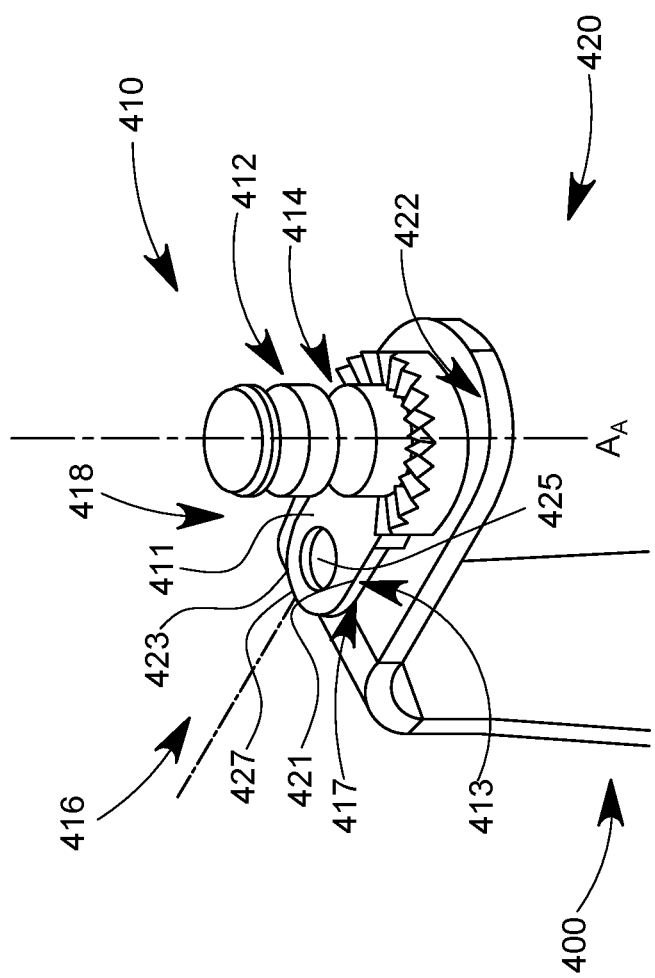
FIG. 3B provides a detailed, perspective view a base portion 420 of the retractor blade of FIG. 2.

As shown in the exploded view of FIG. 3A, the handle assembly 50 may include an attachment portion 60, a handle 70, and a retaining rod 80. The retaining rod 80 may secure the handle 70 to the attachment portion 60. Moreover, the retaining rod 80 may be manipulated to selectably engage the retaining member 630 with the walls 427 of the recess 425.

The attachment portion 60 may be sized and adapted to cooperate with the handle mount 416 of the retractor blade 40. As shown in FIG. 4, the attachment portion 60 may comprise a grooved slot 610 that is sized and adapted to accept and mate with the tab 418 and grooves 417 of the mount 416. The grooved slot 610 and tab 418 may cooperate to secure the attachment portion 60 to the mount 416. To this end, the grooved slot 610 may comprise an upper surface 612 and a lower surface 614. The lower surface 614 may be spaced apart from the upper surface 612 by a distance slightly larger than a thickness of the tab 416. In this manner, the tab 416 may be received by the grooved slot 610 such that the surfaces 612, 614 closely mate and engage the surfaces 411, 413.

Furthermore, the lower surface 612 of the grooved slot 610 may include an opening 616 sized to receive and closely mate with the pedestal 419 upon which the tab 418 rests. The grooved slot 610 may further comprise an end wall 618. The end wall 618 may be sized to receive and closely mate with the rounded or tapered distal end 423 of the tab 418. In particular, the end wall 618 and distal end 423 may cooperate to properly position the tab 418 within the slot 610. In particular, the end wall 618 may stop further advancement of the distal end 423 into the slotted groove 610 when the recess 425 is properly aligned to receive the retaining member 630.

Finally, the upper surface 614 of the groove slot 610 includes an aperture 619. In particular, the aperture 619 is positioned in the upper surface 614 such that the aperture 619 aligns with the recess 425 of the tab 418 when the tab 418 is fully inserted into the slot 610. The aperture 619 is sized to closely mate with a tip 632 of the retaining member 630. As shown, the tip 632 may be beveled or tapered. Such tapering may help guide the tip 632 into the recess 425 even in the presence of minor misalignment of the recess 425 with the aperture 619. For example, a practitioner may fail to fully insert the tab 418 into the slot 610. The tapered tip 632 may aid the member 630 in sliding into the recess 425 and urging the tab 418 into a fully inserted position.

Figure 6:
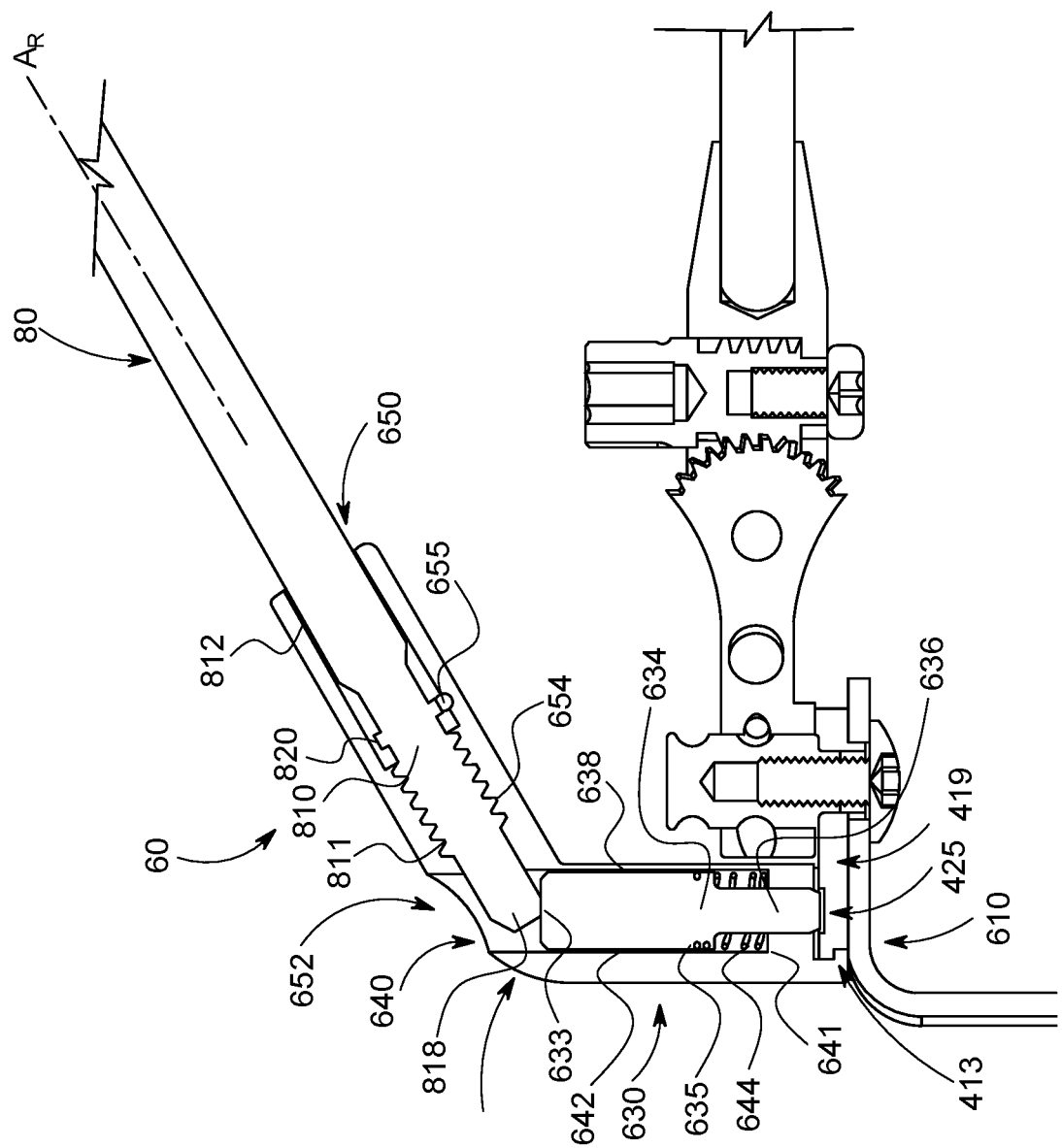
FIG. 6 provides cross-sectional view of the retractor blade of FIG. 2 with the handle assembly in an unlocked position.
Figure 7:
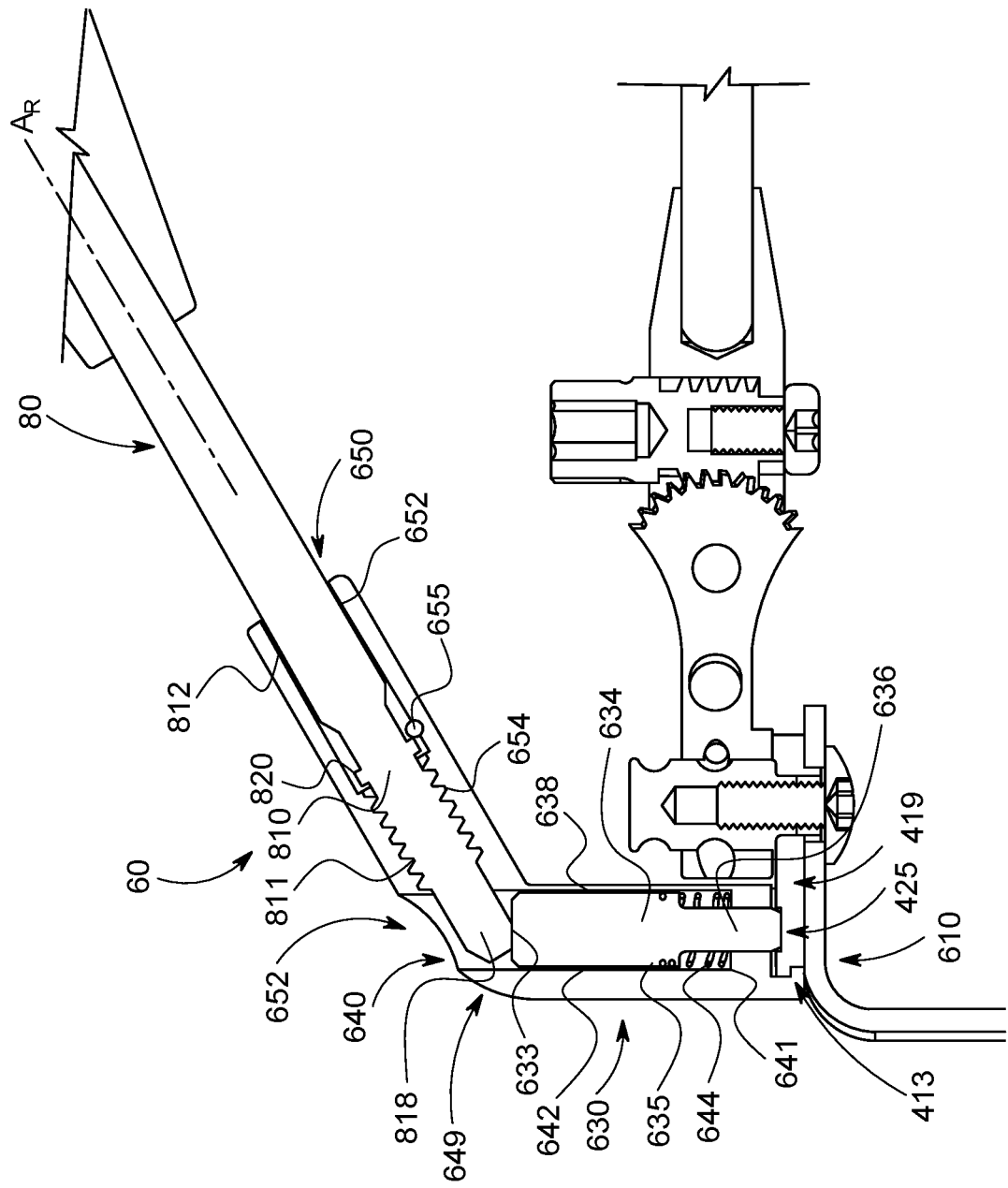
FIG. 7 provides cross-sectional view of the retractor blade of FIG. 2 with the handle assembly in an locked position.

As shown in FIGS. 6 and 7, the retaining member 630 may include a base portion 634 and a peg 636 that extends from the base portion 634. In one embodiment, the both the base portion 634 and peg 636 are cylindrically-shaped with a circular cross-section. The base portion 634, however, may have a larger diameter than the peg 636.

The attachment portion 60 may include a first longitudinal cavity 640 and the retaining member 630 may be housed within such cavity 640. In particular, the cavity 640 may be shaped and sized such that its inner walls 642 closely mate with side walls 638 of the base portion 634 and permit the base portion 634 to slide longitudinally along the cavity 640. As shown in FIG. 6, a spring 644 may be positioned about the peg 636 to bias the retaining member 630 away from the slot 610 and tab 418. To this end, the spring 644 may be compressed between a lower surface 641 of the cavity 640 and a lower surface 635 of the base portion 634.

As further shown in FIGS. 6 and 7, the attachment portion 60 may include a second longitudinal cavity 650 that is sized and adapted to receive a threaded end 810 of the retaining rod 80. As shown, a distal end 652 of the second longitudinal cavity 650 may adjoin a proximal end 649 of the cavity 640. As depicted, the longitudinal axis of the cavity 650 forms an obtuse angle with the longitudinal axis of the cavity 640. The cavity 650 may be shaped and sized such that its inner walls 652 closely mate with side walls 812 of the retaining rod 80 and permit the retaining rod 80 to slide longitudinally along at least a portion of the cavity 650. The inner walls 652 may include threads 654 toward the distal end 652. The threads 654 are configured to engage threads 811 of the retention rod 80.

As a result of such threads 654, 811, the retaining rod 80 may be advanced through the second cavity 650 and into an proximal portion 649 of the first cavity 640 via rotation of the retaining rod 80 in a first direction about a longitudinal axis $A_R$. Conversely, rotation of the retaining rod 80 in a second direction opposite the first direction may withdrawal the rod 80 from the first cavity 640.

As shown in FIG. 6, as the rod 80 is advanced into the first cavity 640, a tapered end 818 of the rod 80 may engage an end 633 of the retaining member 630. Further advancement of the rod 80 may overcome the biasing force of the spring 644 and advance the peg 636 of the retaining member 330 toward the recess 425 of tab 418. As shown in FIG. 7, rod 80 may advance the end 632 of the peg 636 such that the end 632 engages the recess 425, thus preventing withdrawal of the tab 418 from the attachment portion 60. Once in the locked position, an annular rib 820 of rod 80 clears an aperture 655 in the attachment portion 60 that extends laterally into the second cavity 650. A pin 660 may then be inserted into the aperture 655. See, FIG. 3A. The pin 660 may engage and block the passage of the annular rib 820 and thereby prevent withdrawal of the rod 80 from the attachment portion 60. In this manner, the rod 80 may be secured to the attachment portion 60, thus preventing, via the engaged retaining member 630, the detachment of the handle assembly 50 from the retractor blade 40.

The handle 70 may be sized and adapted to be grasped by a practitioner. The handle may include an aperture (not shown) sized to receive a proximal end 830 of the rod 80. As shown in FIG. 3A, the handle 70 may further include an aperture 700 which may be aligned with a corresponding aperture 832 toward the proximal end 830 of the rod 80. Another pin 760 may be passed through the apertures 700, 832 thereby locking the handle 70 to the rod 80. As such, a practitioner may rotate the handle 70 about the longitudinal axis $A_R$ of the rod 80 in order to advance the rod 80 to the retractor blade 40.

Once the handle assembly 50 is secured to the retractor blade 40, the handle 70 provides for convenient manipulation and placement of the retractor blade 40. Once the retractor blade 40 is positioned as desired, the practitioner may remove the pin 660 from the attachment portion 60. The practitioner may then rotate the handle 70 about longitudinal axis $A_R$ to withdrawal the rod 80 from the attachment portion 60 and disengage the retaining member 630 from the mount 416. After such disengagement, the handle assembly 50 may be detached from the retractor blade 40.

To use the retractor system 10, the frame assembly 20 is first secured to the hospital bed. With the patient in place, an incision is made to provide access to the operative site of interest. A retractor blade 40 is then selected and secured to a handle assembly 50. The retractor blade 40 is then inserted, distal end first, into the operative site of interest, and positioned as desired to retract tissue and provide access to the surgical site of interest. Once positioned as desired, the handle assembly 50 may be released from the retractor blade 40. The head 308 of a jointed arm 30 may now be secured to the arm attachment feature 410 of the retractor blade 40, with the first end 302 of the jointed arm 30 secured to the frame assembly 20 with a clamp 26. Thus, the retractor blade 40 is secured at both its distal and proximal ends, removing the need for manual holding of the retractor blade during the procedure.

Further, while the jointed arm 30 generally maintains the retractor blade 40 in position, the motion permitted by the pivot 310 of the jointed arm and/or the interaction between the attachment assembly and the upper groove 412 (if the upper groove 412 is utilized) allows some amount of "float" for the retractor blade 40 relative to the frame assembly 20 in the event of any pounding, chiseling, or other events that may cause portions of the anatomy or equipment to shift, helping to maintain a desired access shape as well as helping to reduce risk of any additional injury or trauma to the patient, as well as damage to any equipment, that may be caused by such a shift or movement. Next, additional retractor blades 40 may be added, positioned, and secured in place as desired. In the embodiment illustrated in FIG. 1, four retractor blades have been used. Each of the retractor blades may be positioned independently of other retractor blades, in contrast to certain known systems that require, for example, paired blades to be located opposed to each other. Thus, the retractor system 10 provides for flexibility in the formation of the desired access site, as well as open access to the site of interest.

While particular embodiments of the invention have been shown, it will be understood that the invention is not limited thereto since modifications may be made by those skilled in the art, particularly in light of the foregoing teaching. It is therefore, the appended claims that define the true spirit and scope of the invention.

What is claimed is:

1. A retractor system, comprising:
   a retractor blade comprising a base portion, a blade extending from the base portion, and a handle mount affixed to the base portion; and
   a handle assembly comprising a rod and an attachment portion that detachably couples the handle assembly to the handle mount of the retractor blade;
   wherein the attachment portion comprises a slot, a first cavity adjoining the slot, a retaining member moveable along the first cavity, a second cavity adjoining the first cavity, and a spring, in the first cavity, that biases the retaining member away from the slot;
   wherein the slot is sized to permit attachment of the handle assembly to the retractor blade via insertion of the handle mount into the slot of the attachment portion and permit detachment of the handle assembly from the retractor blade via withdrawal of the handle mount from the slot of the attachment portion; and
   wherein advancement of the rod through the second cavity and into the first cavity advances the retaining member into a locked position in which the retaining member engages the handle mount in the slot of the attachment portion and prevents withdrawal of the handle mount from the slot of the attachment portion.

2. The retractor system of claim 1, wherein:
   the second cavity comprises threads along an inner wall; and
   the rod comprises threads that, in response to rotation of the rod in a first direction about a longitudinal axis of the rod:
   engage the threads of the second cavity; and
   advance the rod through the second cavity and into the first cavity.

3. The retractor system of claim 2, wherein the threads of the rod, in response to rotation of the rod about the longitudinal axis in a second direction that is opposite the first direction, engage the threads of the second cavity and withdraw the rod from the first cavity.

4. The retractor system of claim 1, wherein the base portion of the retractor blade further comprises an attachment post comprising an annular groove, the attachment post configured to engage an attachment hole of a jointed arm.

5. The retractor system of claim 1, wherein:
the handle mount comprises a recess that aligns with an aperture in a surface of the slot of the attachment portion when the handle mount is received by the slot of the attachment portion; and
the retaining member comprises a peg that extends through the aperture and engages the recess when the retaining member is advanced into the slot of the attachment portion by the rod.

6. The retractor system of claim 1, wherein:
the attachment portion comprises an aperture that extends laterally into the second cavity;
the rod comprises an annular rib that clears the aperture when the rod is fully advanced into the first cavity; and
a pin inserted into the aperture engages the annular rib and prevents withdrawal of the rod from the first cavity.

7. The retractor system of claim 1, further comprising a handle adjoined to an end of the rod.

8. A retractor system, comprising:
a retractor blade comprising a base portion, a blade extending from the base portion, and a handle mount affixed to the base portion; and
a handle assembly comprising an attachment portion detachably coupled to the handle mount of the retractor blade and a rod extending into the attachment portion;
wherein the attachment portion comprises a slot, a spring, and a retaining member;
wherein the rod, when advanced into the attachment portion to a locked position, advances the retaining member into a first position in which the retaining member engages the handle mount in the slot of the attachment portion and prevents withdrawal of the handle mount from the slot of the attachment portion; and
wherein the rod, when withdrawn from the attachment portion to an unlocked position, permits the spring to withdraw the retaining member to a second position in which the retaining member disengages the handle mount in the slot of the attachment portion and permits detachment of the attachment portion from the handle mount of the retractor blade.

9. The retractor system of claim 8, wherein:
the attachment portion comprises threads along an inner wall; and
the rod comprises threads that engage the threads of the attachment portion.

10. The retractor system of claim 9, wherein the threads of the rod, in response to rotation of the rod about a longitudinal axis, engage the threads of the attachment portion and withdraw the rod away from the retaining member.

11. The retractor system of claim 8, wherein:
the handle mount comprises a recess; and
the retaining member comprises a peg that engages the recess and prevents detachment of the attachment portion of the handle assembly from the handle mount of the retractor blade.

12. The retractor system of claim 8, further comprising a jointed arm secured to the base portion of the retractor blade.

13. The retractor system of claim 8, further comprising a jointed arm secured to an attachment post on the base portion of the retractor blade.

14. The retractor system of claim 13, further comprising a frame, wherein the jointed arm is secured to the frame.

15. A retractor system, comprising:
a retractor blade comprising a base portion, a blade extending from the base portion, and a handle mount affixed to the base portion; and
a handle assembly comprising an attachment portion detachably coupled to the handle mount of the retractor blade and a rod extending into the attachment portion;
wherein the attachment portion comprises a slot and a retaining member;
wherein the rod advances the retaining member into a locked position in which the retaining member engages the handle mount of the retractor blade in the slot of the attachment portion and prevents withdrawal of the handle mount of the retractor blade from the slot of the attachment portion; and
wherein the attachment portion further comprises a spring configured to move and disengage the retaining member from the handle mount of the retractor blade as the rod is moved away from the retaining member.

16. The retractor system of claim 15, wherein:
the attachment portion comprises threads along an inner wall; and
the rod comprises threads that engage the threads of the attachment portion.

17. The retractor system of claim 16, wherein the threads of the rod, in response to rotation of the rod about a longitudinal axis, engage the threads of the attachment portion and withdraw the rod away from the retaining member.

18. The retractor system of claim 15, wherein:
the attachment portion comprises an aperture;
the rod comprises an annular rib that clears the aperture when the rod is fully advanced into the attachment portion; and
a pin inserted into the aperture engages the annular rib and prevents withdrawal of the rod from the attachment portion.

19. The retractor system of claim 15, further comprising a handle adjoined to an end of the rod.

* * * * *